(12) United States Patent
Lin et al.

(10) Patent No.: US 6,454,996 B1
(45) Date of Patent: Sep. 24, 2002

(54) METHOD FOR TREATING AGRICULTURAL PRODUCTS FOR HARMFUL INFESTATIONS

(75) Inventors: James C. Lin, Orinda, CA (US); Hidemasa Toyoshima, Shizuoka (JP)

(73) Assignee: Lin Cubing Inc., Orinda, CA (US)

( * ) Notice: Subject to any disclaimer, the term of this patent is extended or adjusted under 35 U.S.C. 154(b) by 0 days.

(21) Appl. No.: 09/257,429

(22) Filed: Feb. 24, 1999

(51) Int. Cl.⁷ ................................................ A61L 2/07
(52) U.S. Cl. ........................... 422/26; 422/22; 422/23; 19/66 R; 426/242
(58) Field of Search ..................... 422/32, 33, 21, 422/22; 426/242, 520; 19/66 R (56) References Cited

U.S. PATENT DOCUMENTS

| | | | |
|---|---|---|---|
| 4,064,276 A | * | 12/1977 | Conradsen et al. ............ 426/69 |
| 4,144,354 A | * | 3/1979 | Unno et al. .................... 426/2 |
| 4,471,790 A | * | 9/1984 | Davis, Jr. et al. ............ 131/301 |
| 4,627,338 A | * | 12/1986 | Sprott et al. .................... 99/534 |
| 4,922,933 A | * | 5/1990 | Jakob .......................... 131/299 |
| 4,942,717 A | * | 7/1990 | Kozub .......................... 53/428 |
| 5,141,059 A | * | 8/1992 | Marsh ............................ 172/1 |
| 5,523,053 A | * | 6/1996 | Dudek .......................... 422/26 |
| 5,799,572 A | * | 9/1998 | Campbell et al. ............. 100/38 |
| 5,855,857 A | * | 1/1999 | Dithmer ...................... 422/307 |

* cited by examiner

Primary Examiner—Robert J. Warden, Sr.
Assistant Examiner—Sean E. Conley
(74) Attorney, Agent, or Firm—Lyon & Lyon LLP (57) ABSTRACT

A method for treating agricultural products for insects, microorganisms, and other infestations is disclosed. An aspect of the method entails reducing or increasing the air pressure associated with the agricultural product, then introducing one or more treatments to the agricultural product. One treatment may comprise heat, and the heat may be in the form of steam or heated air. A second treatment may comprise electromagnetic radiation, in the form of microwave energy or high frequency waves.

32 Claims, 5 Drawing Sheets

METHOD FOR TREATING AGRICULTURAL PRODUCTS FOR HARMFUL INFESTATIONS

BACKGROUND OF THE INVENTION

1. Field of the Invention

The present invention pertains generally to the field of agricultural products. More specifically, the present invention pertains to methods of treating agricultural products for the elimination of harmful infestations.

2. Description of Related Art

Agricultural products may contain the presence of insects, microorganisms, and other infestations including but not limited to bacteria, viruses, and other pathogenic organisms. These insects, microorganisms, and other infestations may cause harmful effects if they are transmitted to other plants and crops, or if the agricultural products containing these infestations are consumed by humans or livestock. To provide an example, harmful infestations are a known concern for bales of hay, and more specifically, bales of rice straw (a type of hay). Bales of hay, particularly bales of rice straw, are consumed in large quantities by livestock raised all over the world. Often, the bales of hay are produced in one part of the world, and are transported across national or regional borders to be consumed in other parts of the world. However, many countries impose severe restrictions upon the importation of hay due to the possible presence of bacteria or other harmful microorganisms. This due in great part to the desire to prevent certain types of harmful bacteria from being brought into those respective countries. Cochliobolus miyabearus is one example of such a bacteria that may be present within bales of hay which the import restrictions are designed to prevent being imported.

A number of different approaches can be taken to treat hay such that the harmful insects, microorganisms, and other infestations are destroyed. One such approach is to apply dry heat to bales of hay in an effort to increase the temperature of the hay to a high enough level to kill the harmful infestations. This can be done by placing the bales of hay inside an oven to heat the hay to an adequate temperature. For instance, some bacteria, such as cochliobolus miyabearus, may need to be heated to temperatures in excess of 80° C. to be destroyed. One drawback to this method is that because hay is normally packaged in bales of fairly large size and density, it can take a long time for every part of the bale of hay, particularly all of the areas within the internal regions of the bale of hay (such as the core), to reach the proper temperature. Depending upon the size and density of the bales of hay being treated, several hours may be needed to treat the hay such. that the entire bale, including its core, reaches the proper temperature. This places a severe bottleneck upon the treatment of large quantities of bales of hay.

The use of microwave energy to heat bales of hay is another approach that can be taken to treat the hay for possible infestations. The drawback to this method is that the hay is not uniformly heated over and within the entire bale of hay, and therefore some portions of the bale of hay may not achieve adequate temperature levels. Thus, some of the harmful infestations may not be destroyed by the treatment.

The use of chemicals to treat the bales of hay is yet another approach that can be taken to treat the hay. However, one significant drawback to this approach is that conventional chemicals used to treat agricultural products do not affect or destroy certain types of harmful infestations. Another drawback is that the chemically treated hay may be unsatisfactory for consumption by cows or other livestock.

Accordingly, there exists a need for a process to address these and other problems relating to the treatment of agricultural products. There exists a need for a process to effectively and efficiently destroy harmful insects, microorganisms, and other infestations, including but not limited to bacteria, viruses, and other pathogenic organisms, present in and on bales of hay.

SUMMARY OF THE INVENTION

The present invention comprises a method of treating agricultural products for insects, microorganisms, and other infestations, including but not limited to bacteria, viruses, and other pathogenic organisms.

An aspect of the invention involves reducing the air pressure associated with the agricultural product, for example, a bale of hay. This entails reducing the air pressure either within the agricultural product, around the agricultural product, or both within and around the agricultural product. Preferably, the pressure reduction will be created both within and around the agricultural product. According to an embodiment, heat is then applied to the agricultural product. The heat may be applied in combination with the application of another treatment, such as electromagnetic radiation energy. This procedure can then be repeated, if necessary, from once to several times. The number of cycles of this process that one would need to go through in order to achieve the correct temperature will depend upon the size and density of the bale of hay being treated.

These and other objects and advantages of the present invention will become apparent to those of ordinary skill in the art from a consideration of the drawings and the description of the process contained herein. The principles of the present process may be employed in any agricultural application.

DESCRIPTION OF THE PREFERRED EMBODIMENTS

The invention is directed to a method for treating agricultural products that may contain insects, microorganisms, and other infestations, including but not limited to bacteria, viruses, and other pathogenic organisms. For purposes of illustration, and not by way of limitation, the present specification shall describe the invention with reference to the treatment of bales of hay. However, the invention is equally applicable to the treatment of other agricultural products.

According to an embodiment of the invention, the method comprises the reduction of air pressure associated with a bale of hay 15. This reduction of air pressure occurs either within the bale of hay, around the bale of hay, or both within and around the bale of hay. Preferably, the pressure reduction will be created both within and around the bale of hay. Once the air pressure has been reduced, one or more treatments are applied to the bale of hay to destroy harmful infestations.

Figure 1A:
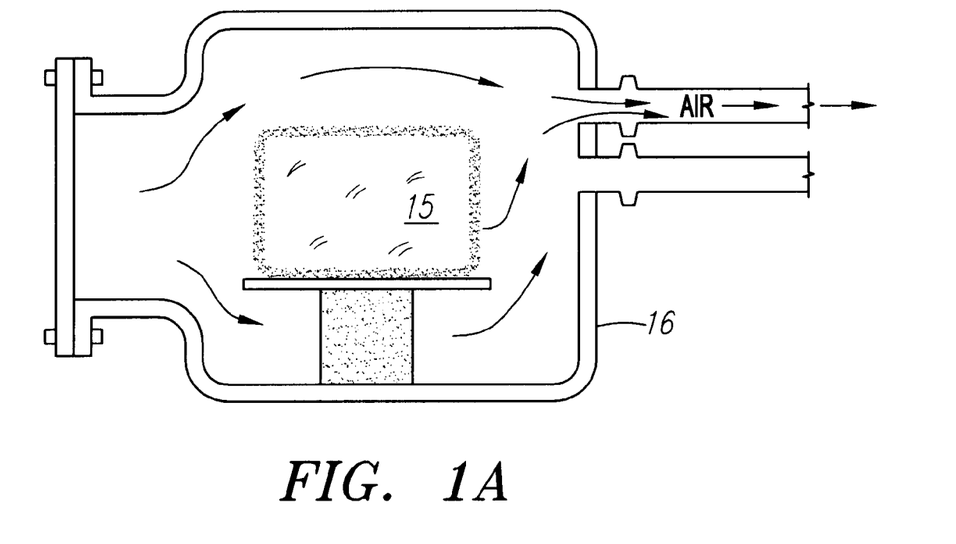
FIG. 1A illustrates an agricultural product within a vessel, while the air within the vessel is drawn out.
Figure 1B:
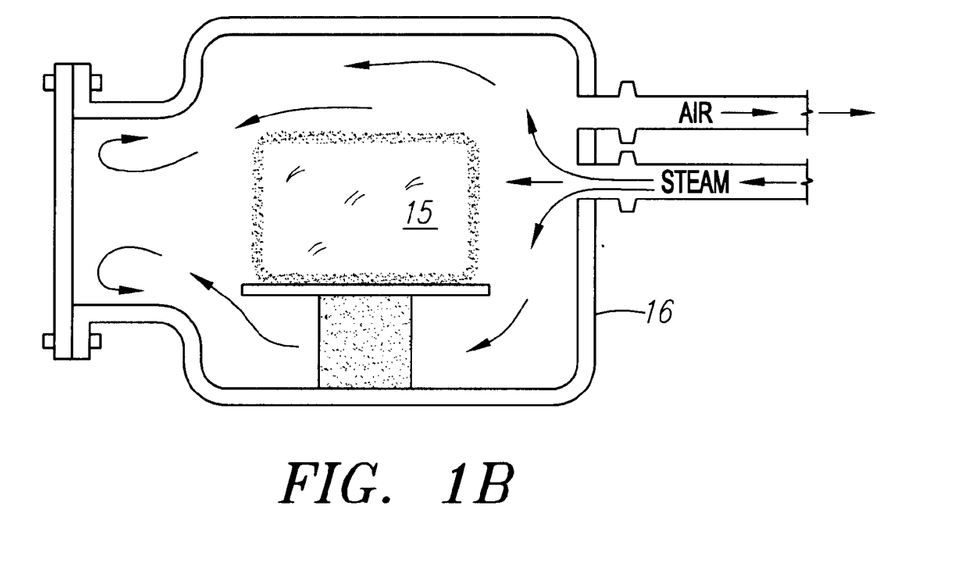
FIG. 1B illustrates heat in the form of steam being added to the interior of a vessel.
Figure 1C:
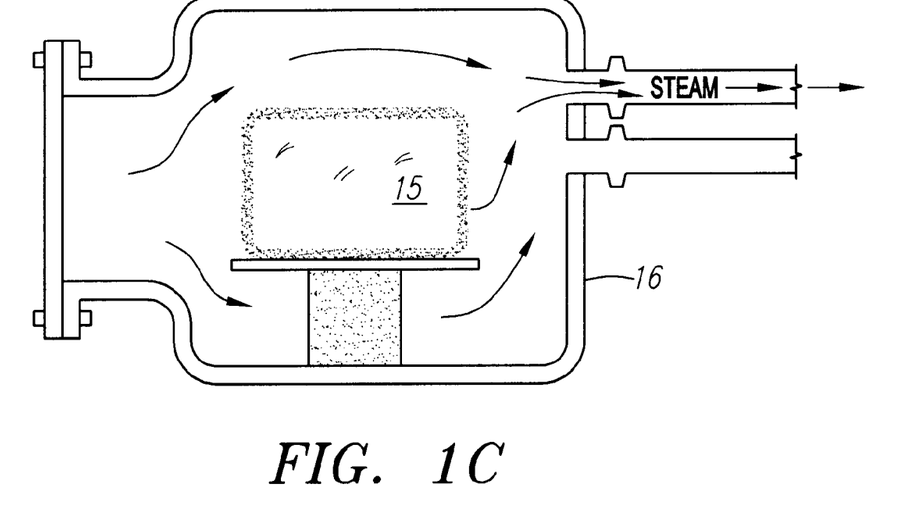
FIG. 1C illustrates the steam being withdrawn from a vessel.

FIGS. 1A–C depict a bale of hay 15 undergoing treatment according to an embodiment of the invention. Bale of hay 15 is completely enclosed within a pressure vessel 16. The pressure vessel 16 is one that is capable of withstanding pressure changes within its interior, such as a reduction or increase in pressure. The pressure vessel 16 is also one that has at least one, preferably two or more conduits, such as pipelines, that extend from the pressure vessel 16. The conduits allow air to be removed from within the interior of the pressure vessel 16, and allow air, dry heat, steam, chemicals, or other treatments to be introduced into the pressure vessel 16, all while the pressure vessel 16 is sealed. The pressure vessel 16 preferably has a mechanism for measuring the pressure within its interior, such as a pressure gauge or pressure transmitter. In an embodiment, the pressure vessel 16 also includes conduits for allowing wires to pass from the interior of the vessel to the exterior without affecting the operation of the pressure vessel 16. These wires are used to operate and gather data from instruments within the pressure vessel 16, for example pressure transmitters, thermometers, thermocouples, and other pressure measuring and temperature measuring devices. Pressure vessels used in the textile industry for the treatment of fabrics with dyes are suitable for use in the present invention.

Turning to FIG. 1A, after the bale of hay 15 is placed inside the pressure vessel 16 and the vessel 16 is sealed, the pressure inside the vessel 16 is reduced. The amount of air pressure reduction within the vessel 16 will depend upon the size and density of the bale of hay 15 being treated. For example, according to one implementation of the invention, a bale of rice straw hay that measures 25 cm×30 cm×70 cm and has a density of approximately 400–500 kg/m$^3$ will be sufficiently treated when the pressure is reduced to approximately 720–750 mmHg within the vessel.

Turning to FIG. 1B, once the pressure has been sufficiently reduced, a treatment is added to the interior of the pressure vessel 16. The preferred treatment is heat, wherein the applied heat comprises steam. According to one embodiment, steam is added at 100° C., although steam at other temperatures may be utilized. For example, superheated steam may be used in an alternate embodiment of the invention. Alternate sources of heat include dry heat, which is air that has been heated, other gases, substances, or chemicals that have been heated, and electromagnetic radiation energy. An alternate embodiment may use a chemical that is capable of killing the insects, microorganisms, and other infestations present in and on the agricultural product being treated.

Thermocouples, thermocouple-thermowell assemblies, thermometers, or other temperature sensing devices inside the vessel may be used to monitor temperatures at various locations on and within the bale of hay. For example, thermocouples or thermocouple-thermowell assemblies may be inserted into various parts of the bale of hay, including its core, to monitor temperatures throughout the bale of hay during this process. This is done in order to determine whether the various parts of the bale of hay reached adequate temperatures for the treatment to be effective.

Turning to FIG. 1C, the treatment, in this case steam, is allowed to remain in the vessel for a time period. The exact amount of time the steam remains inside the vessel will depend upon the size and density of the agricultural product being treated. In an embodiment, for bales of rice straw hay that measure 25 cm×30 cm×70 cm and have a density of approximately 400–500 kg/m$^3$, the steam is allowed to remain in the vessel for approximately five minutes. Next the steam is released from the pressure vessel 16. This entire process can then be repeated if any area on or within the bale of hay did not reach an adequate temperature for the treatment to be effective. The number of times that the bale of hay is subjected to the "reduce pressure-add steam-release steam" cycle depends upon the size and density of the hay. The bigger the bale of hay, or the more dense the bale of hay is, the more cycles may be required in order to ensure that the core of the bale of hay is heated to the correct temperature in order that the bacteria be effectively destroyed. Alternatively, the cycle can be performed only a single time, for a period of time large enough for the entire bale of hay to reach an adequate temperature.

Figure 1D:
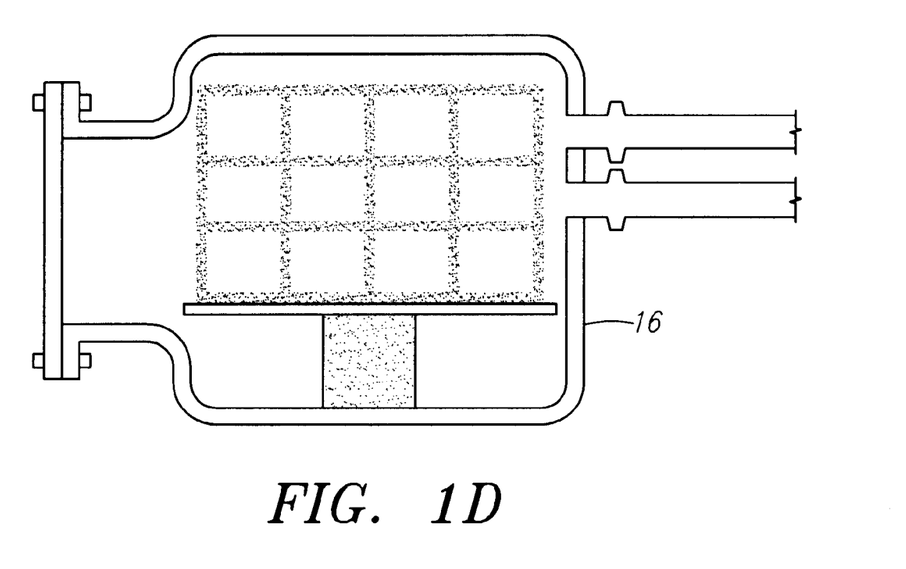
FIG. 1D illustrates the treatment of several bales of hay within a pressure vessel.

This process can be applied to simultaneously treat multiple bales of hay. FIG. 1D illustrates the pressure vessel 16 holding several bales of hay concurrently.

Figure 2A:
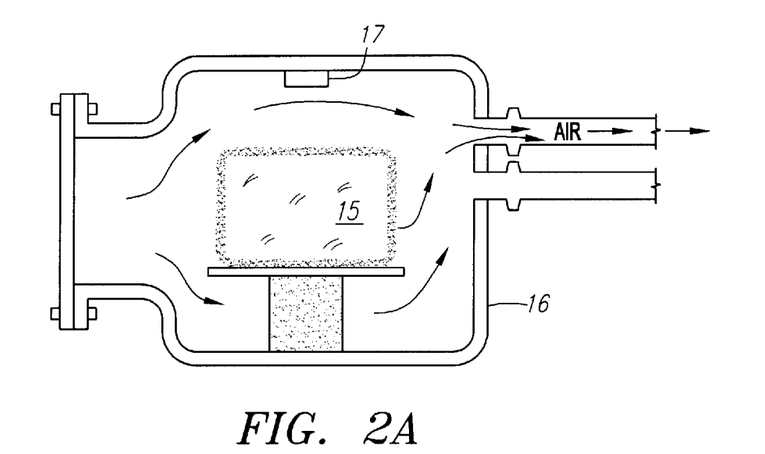
FIG. 2A illustrates an agricultural product within a vessel, while the air within the vessel is drawn out.
Figure 2B:
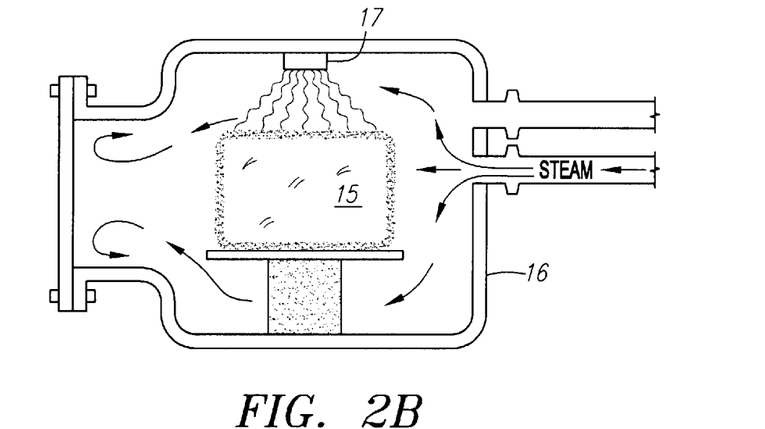
FIG. 2B illustrates heat in the form of steam being added to the interior of a vessel, while contemporaneously, electromagnetic radiation in the form of microwave energy is applied to the agricultural product.
Figure 2C:
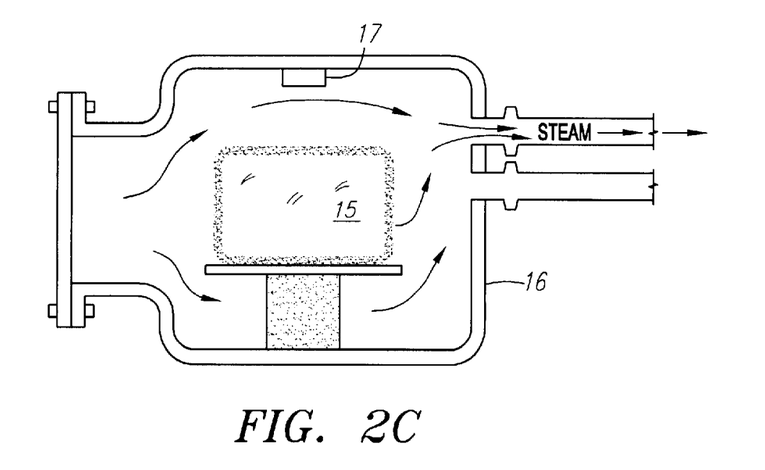
FIG. 2C illustrates the steam being withdrawn from a vessel and the application of microwave energy ceasing.

Turning to FIGS. 2A–C, according to another embodiment of the invention, the method comprises the application of two or more forms of treatment simultaneously to the agricultural product while it is inside the pressure vessel and after the pressure within the vessel has been reduced. A first treatment may comprise heat, preferably in the form of steam. A second treatment may comprise electromagnetic radiation energy, preferably in the form of microwave energy or high frequency waves. Again, a bale of hay 15 is used for purposes of illustration and not by way of limitation.

Turning to FIG. 2A, the agricultural product, for example a bale of hay 15, is placed in a pressure vessel 16 and the pressure vessel is sealed. Then the pressure within the vessel is reduced. Again, the amount of pressure reduction within the pressure vessel 16 will depend upon the size and density of the agricultural product being treated.

Turning to FIG. 2B, two treatments are applied to the bale of hay 15. The first treatment is heat in the form of steam, and the second treatment is electromagnetic radiation energy, in the form of microwave energy. The microwave energy emanates from the microwave radiation source 17.

Turning to FIG. 2C, the application of microwave radiation is stopped and the steam is released from the pressure vessel 16. As discussed above, this process can then be repeated, if necessary, if any area on or within the bale of hay did not reach an adequate temperature for the treatment to be effective. Alternatively, the cycle can be performed only a single time, for a period of time large enough for the entire bale of hay to reach an adequate temperature.

Figure 3:
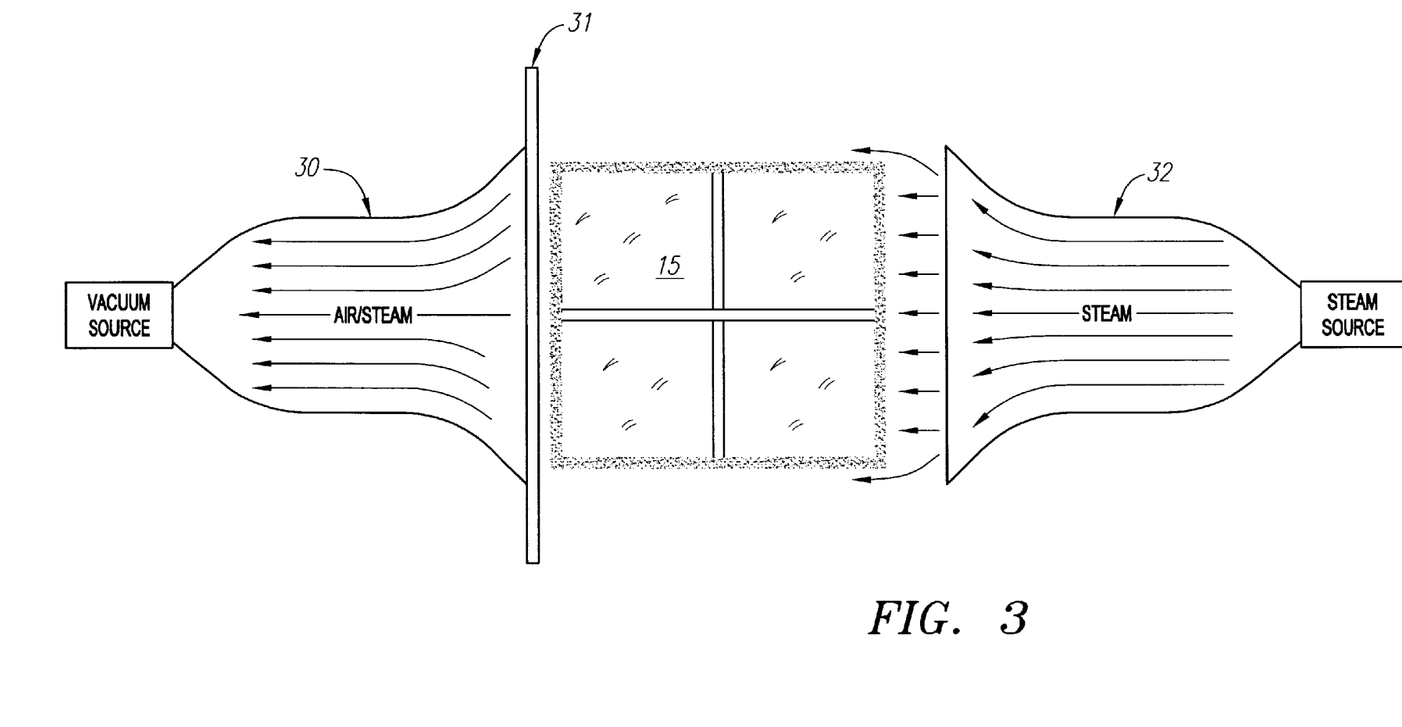
FIG. 3 illustrates an alternate embodiment of the invention.

Now turning to FIG. 3, according to another embodiment of the invention, the method again comprises the reduction of air pressure associated with the agricultural product, but utilizing a different process. Again, for purposes of illustration and not by way of limitation, a bale of hay 15 is shown as the agricultural product being treated.

In this embodiment, at one end of the bale of hay 15 exists a vacuum source 30 that withdraws air from within and, around the bale of hay 15. The vacuum source 30 is an apparatus that is capable of drawing air away from the bale of hay, such as a vacuum pump or venturi, and does not necessarily create a total vacuum on the agricultural product. The vacuum source 30 may be used on the bale of hay 15 in conjunction with a screen assembly 31, located between the vacuum source 30 and the bale of hay 15. The screen assembly 31 is used to prevent the bale of hay 15 from entering the vacuum source 30.

At the opposite end of the bale of hay 15, a treatment source 32 is present. The treatment source 32 provides a treatment for the agricultural product. The treatment is preferably heat in the form of steam, dry heat, or an alternate source of heat, but may also comprise a chemical treatment. For purposes of illustration and not by way of limitation, the description of this embodiment will use steam heat as the form of treatment.

When the vacuum source 30 withdraws air from within and around the bale of hay 15, the pressure within and around the bale of hay 15 is consequently reduced. As air is withdrawn from the bale of hay 15, the treatment source 32 applies steam to the bale of hay 15. This causes the steam to be drawn into and around the bale of hay 15. As the steam is drawn into all parts of the bale of hay 15, heat is accordingly applied throughout the bale of hay and raises the temperature of the various parts of the bale of hay to levels adequate for destroying the insects, microorganisms, and other infestations present in the bale of hay.

Figure 4A:
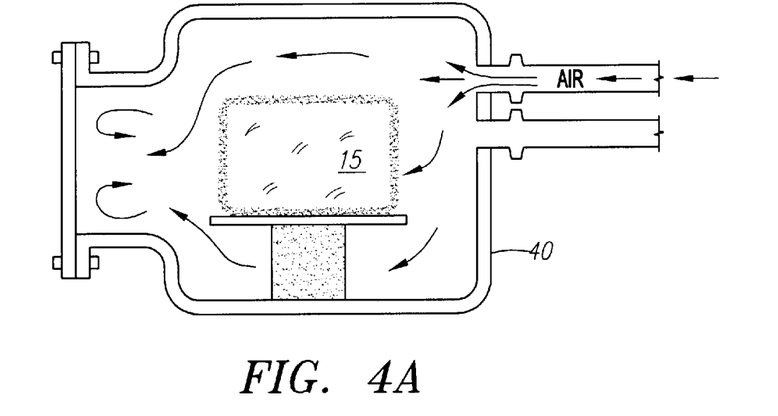
FIG. 4A illustrates an agricultural product within a vessel, while the pressure within the vessel is increased.
Figure 4B:
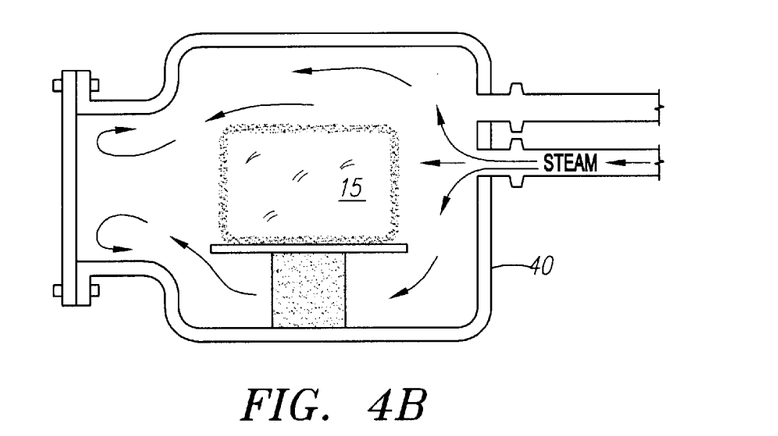
FIG. 4B illustrates heat being added to the interior of a vessel.
Figure 4C:
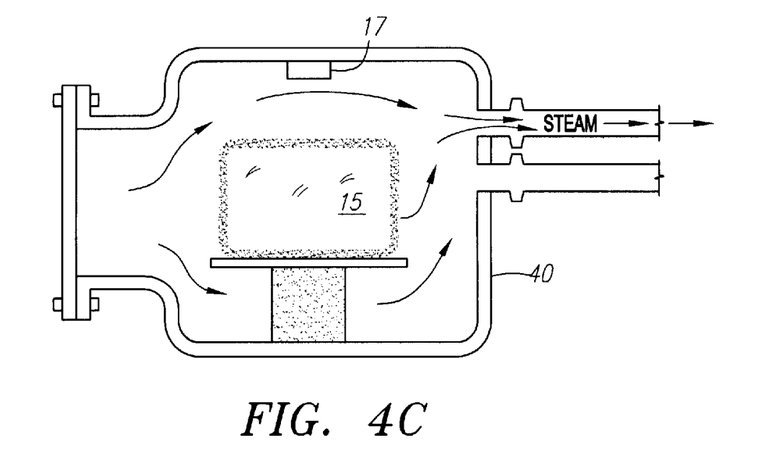
FIG. 4C illustrates the heat being withdrawn from a vessel.

In another embodiment of the invention, the method comprises the increase of air pressure associated with an agricultural product. Again, for purposes of illustration and not by way of limitation, a bale of hay will be referred to as the agricultural product being treated. FIGS. 4A–C illustrate a bale of hay 15 undergoing treatment according to this embodiment of the invention. Bale of hay 15 is completely enclosed within a pressure vessel 40. The pressure vessel 40 is able to withstand increases in air pressure within its interior. The description of the pressure vessel 16 used earlier in this specification is applicable to the type of pressure vessel that may be used in this embodiment.

Turning to FIG. 4A, once the bale of hay 15 is placed inside the pressure vessel 40, the pressure is increased within the pressure vessel 40. The increase of air pressure occurs either within the bale of hay, around the bale of hay, or both within and around the bale of hay.

Turning to FIG. 4B, once the pressure associated with the bale of hay is sufficiently increased, a treatment is added to the interior of the pressure vessel 40. The treatment is preferably heat, but may also be a chemical treatment. For heat treatments, the heat can be applied using a variety of heat sources, with a preferred one being steam at 100° C. The use of dry heat or other gases that have been heated is also acceptable.

Turning to FIG. 4C, after a period of time, the steam is released from the pressure vessel 40. This entire process can then be repeated if any area on or within the bale of hay did not reach an adequate temperature for the treatment to be effective. The use of temperature measuring devices, such as thermometers, thermocouples, or thermocouple-thermowell assemblies, within the pressure vessel 40, inserted into various parts of the bale of hay 15, will provide data on which areas of the bale of hay 15 were sufficiently heated. As with the previous embodiments, the number of times that the bale of hay is subjected to the "increase pressure-add steam-release steam" cycle depends upon the size and density of the hay. The bigger or more dense the bale of hay is, the more cycles may be required in order to ensure that the core of the bale of hay is heated to the correct temperature in order for the insects, microorganisms and other infestations to be effectively destroyed. Alternatively, the cycle can be performed only a single time for a period of time large enough for the entire bale of hay to reach an adequate temperature.

In another embodiment, the pressure inside the vessel may be increased and heat introduced, as in the preceding embodiment, but here a second treatment may be introduced concurrently with the heat treatment. Such a second treatment may comprise electromagnetic radiation in the form of microwave energy.

According to another embodiment of the invention, the method again uses a pressure vessel in which to create the change in pressure associated with the agricultural product. The difference is that this embodiment utilizes an alternate method for introducing heat to the agricultural product being treated. In this embodiment, the pressure vessel is jacketed, thereby permitting the wall of the pressure vessel to be heated. This heated jacket will in turn provide heat to the interior of the vessel and consequently to the agricultural product contained inside the vessel. The jacket on the pressure vessel can use a variety of mediums for a heat supply, for example electrical tracing, heated water, or steam.

The heat from the walls of the vessel will be conducted to the agricultural product by either the air that remains in the vessel once the pressure is reduced, or by another medium, such as another gas that is introduced or is present inside the vessel.

According to yet another embodiment of the invention, which is a variation on the preceding embodiment, the method comprises using a shell and tube heat exchanger as the pressure vessel. The heating medium flows shell-side, while the agricultural product to be treated is placed tube-side. In one embodiment, the pressure tube-side is decreased to a level where the agricultural product will be effectively treated. In another embodiment, the pressure tube-side is increased to a level where the agricultural product will be effectively treated. Again, the amount of reduction or increase in pressure adequate for the treatment to be effective will be dependent upon the size and density of the agricultural product being treated.

On the shell-side of the heat exchanger, a heating medium such as steam, heated water, heated air, or another heated gas or substance will flow in order to provide heat to the tube-side agricultural product.

While embodiments, applications, and advantages of the invention have been shown and described with sufficient clarity to enable one skilled in the art to make and use the invention, it would be equally apparent to those skilled in the art that many more embodiments, applications and advantages are possible without deviating from the inventive concepts disclosed and described herein. The invention therefore should only be restricted in accordance with the spirit of the claims appended hereto and is not to be restricted by the preferred embodiments, specification, or drawings.

What is claimed is:

1. A process for treating a baled agricultural product, comprising:

placing said baled agricultural product into a pressure vessel;

reducing pressure within said pressure vessel;

introducing a first treatment to said baled agricultural product, said first treatment comprising heat treatment;

measuring an internal temperature of said baled agricultural product; and continuing said heat treatment until said internal temperature reaches a temperature level of approximately 100 degrees Celsius.

2. The process of claim 1, wherein said heat treatment comprises steam.

3. The treatment of claim 2, wherein said steam is released from said pressure vessel and the steps of adding steam and releasing steam from said pressure vessel are repeated until said temperature level is achieved.

4. The process of claim 1, further comprising:

continuing said heat treatment until for a specified period of time.

5. The process of claim 4 wherein said specified period of time comprises approximately 5 minutes.

6. The process of claim 4 in which said heat treatment is repeated.

7. The process of claim 6 in which said heat treatment is repeated to achieve said temperature level for said internal temperature.

8. The process of claim 1 wherein said internal temperature is measured at a core of said baled agricultural product.

9. The process of claim 1, further comprising:

introducing a second treatment to said baled agricultural product, said second treatment comprising a chemical treatment.

10. The process of claim 1, wherein said baled agricultural product comprise hay.

11. The process of claim 10, wherein said hay comprises rice straw.

12. The process of claim 1 further comprising increasing said pressure within said pressure vessel and repeating the steps of reducing and increasing said pressure.

13. The process of claim 1, wherein said internal temperature is maintained at said temperature level for a period of time projected to destroy said harmful infestation.

14. The process of claim 1, further comprising measuring said internal temperature using a thermocouple.

15. The process of claim 1, further comprising measuring said internal temperature using a thermocouple-thermowell assembly.

16. A process for treating a baled agricultural product, comprising:

placing said baled agricultural product into a pressure vessel;

reducing pressure to approximately 720–750 mmHg within said pressure vessel;

introducing a first treatment to said baled agricultural product, said first treatment comprising heat treatment;

measuring an internal temperature of said baled agricultural product; and continuing said heat treatment until said internal temperature reaches a temperature level projected to destroy harmful infestation.

17. A process for treating a baled agricultural product, comprising:

placing said baled agricultural product into a pressure vessel;

reducing pressure within said pressure vessel;

introducing a first treatment to said baled agricultural product, said first treatment comprising heat treatment, said heat treatment further comprising steam at least 100 degrees Celsius in temperature;

measuring an internal temperature of said baled agricultural product; and continuing said heat treatment until said internal temperature reaches a temperature level projected to destroy a harmful infestation.

18. A process for treating a baled agricultural product, comprising:

placing said baled agricultural product into a pressure vessel;

reducing pressure within said pressure vessel;

introducing a first treatment to said baled agricultural product, said first treatment comprising heat treatment, said heat treatment further comprising heated air;

measuring an internal temperature of said baled agricultural product; and continuing said heat treatment until said internal temperature reaches a temperature level projected to destroy a harmful infestation.

19. A process for treating a baled agricultural product, comprising:

placing said baled agricultural product into a pressure vessel;

reducing pressure within said pressure vessel;

introducing a first treatment to said baled agricultural product, said first treatment comprising heat treatment;

measuring an internal temperature of said baled agricultural product;

continuing said heat treatment until said internal temperature reaches a temperature level projected to destroy a harmful infestation; and introducing a second treatment to said baled agricultural product, said second treatment comprising electromagnetic radiation.

20. The process of claim 19, wherein said electromagnetic radiation comprises microwaves.

21. The process of claim 19, wherein said electromagnetic radiation comprises high frequency waves.

22. An apparatus for treating a baled agricultural product, comprising:

a pressure vessel, said pressure vessel having an interior sufficiently sized to enclose one or more baled agricultural products;

a pressure measuring mechanism to measure pressure within said interior of said pressure vessel;

a heat treatment mechanism to apply heat to said interior of said pressure vessel, said heat having a temperature level of approximately 100 degrees Celsius; and a temperature measuring mechanism to measure an internal temperature of a baled agricultural product that is placed within said interior of said pressure vessel.

23. The apparatus of claim 22, in which said pressure monitoring mechanism comprises a pressure gauge.

24. The apparatus of claim 22, in which said pressure monitoring mechanism comprises a pressure transmitter.

25. The apparatus device of claim 22, in which the heat treatment mechanism comprises a conduit for introducing steam into said interior of said pressure vessel.

26. The apparatus of claim 22, wherein said temperature measuring mechanism comprises a thermocouple capable of being at least partially inserted into a baled agricultural product.

27. The device of claim 22, wherein said temperature measuring mechanism comprises an insertable thermocouple-thermowell assembly capable of being at least partially inserted into a baled agricultural product.

28. The apparatus of claim 22, wherein said temperature measuring mechanism comprises an insertable thermometer.

29. The apparatus of claim 22, further comprising a chemical treatment device.

30. An apparatus for treating a baled agricultural product, comprising:
- a pressure vessel, said pressure vessel having an interior sufficiently sized to enclose one or more baled agricultural products;
- a pressure measuring mechanism to measure pressure within said interior of said pressure vessel;
- a heat treatment mechanism to apply heat to said interior of said pressure vessel;
- a temperature measuring mechanism to measure an internal temperature of a baled agricultural product that is placed within said interior of said pressure vessel; and
- an electromagnetic energy device.

31. The apparatus of claim 30 in which the electromagnetic energy device generates microwave energy.

32. The apparatus of claim 30 in which the electromagnetic energy device generates high frequency waves.

* * * * *